United States Patent
Lee (10) Patent No.: US 11,365,406 B2
(45) Date of Patent: Jun. 21, 2022

(54) FIXED TUBE OF NUCLEIC ACID EXTRACTION COMPONENT, AND NUCLEIC ACID EXTRACTION COMPONENT

(71) Applicant: CATCHGENE CO., LTD., New Taipei (TW)

(72) Inventor: Te-Cheng Lee, New Taipei (TW)

(73) Assignee: CATCHGENE CO., LTD., New Taipei (TW)

( * ) Notice: Subject to any disclaimer, the term of this patent is extended or adjusted under 35 U.S.C. 154(b) by 217 days.

(21) Appl. No.: 16/626,834

(22) PCT Filed: Jun. 5, 2018

(86) PCT No.: PCT/CN2018/089930
§ 371 (c)(1),
(2) Date: Dec. 26, 2019

(87) PCT Pub. No.: WO2019/001228
PCT Pub. Date: Jan. 3, 2019

(65) Prior Publication Data
US 2020/0131503 A1    Apr. 30, 2020

(30) Foreign Application Priority Data
Jun. 30, 2017 (CN) .......................... 201710519911.9

(51) Int. Cl.
*C12N 15/10* (2006.01)
*B01D 63/08* (2006.01)
(Continued)

(52) U.S. Cl.
CPC ......... *C12N 15/1017* (2013.01); *B01D 63/08* (2013.01); *B01D 63/16* (2013.01);
(Continued)

(58) Field of Classification Search
CPC ........... C12N 15/1017; C12N 15/1006; B01D 63/08; B01D 63/16; B01D 2313/06;
(Continued)

(56) References Cited

U.S. PATENT DOCUMENTS

| | | | |
|---|---|---|---|
| 2003/0091989 A1 | 5/2003 | Davis et al. | |
| 2014/0018529 A1* | 1/2014 | Perry | B01L 3/5023 536/25.41 |
| 2015/0289856 A1* | 10/2015 | Saqi | A61M 1/3403 422/534 |

FOREIGN PATENT DOCUMENTS

| | | |
|---|---|---|
| CN | 203846026 U | 9/2014 |
| CN | 203947102 | * 11/2014 |

(Continued)

*Primary Examiner* — Benjamin R Whatley
*Assistant Examiner* — Jacqueline Brazin
(74) *Attorney, Agent, or Firm* — Muncy, Geissler, Olds & Lowe, P.C.

(57) ABSTRACT

A fixed tube of a nucleic acid extraction component and a nucleic acid extraction component. The nucleic acid extraction component includes a membrane column, which is fitted over the fixed tube. The fixed tube has a tube body, a tube opening, and a bottom. The tube body extends along a first direction. The end of the tube opening distal from the tube body has a protrusion which protrudes along a second direction, the first direction being vertical to the second direction. The bottom and the tube opening are respectively connected to two opposite sides of the tube body. The bottom has a shoulder and the shoulder of the bottom is connected to the membrane column.

13 Claims, 11 Drawing Sheets

(51) Int. Cl.
  *B01D 63/16* (2006.01)
  *B01L 3/00* (2006.01)
(52) U.S. Cl.
  CPC ........ *B01L 3/5082* (2013.01); *B01D 2313/06* (2013.01); *B01D 2313/20* (2013.01); *B01L 2200/0647* (2013.01); *B01L 2300/06* (2013.01)
(58) Field of Classification Search
  CPC ............ B01D 2313/20; B01D 2323/20; B01D 2325/16; B01D 71/024; B01D 63/087; B01L 3/5082; B01L 2200/0647; B01L 2300/06; B01L 2300/043; B01L 2300/0681; B01L 3/5021; B01L 2200/0631; B01L 3/50255; C12Q 1/6806
  USPC ........................................................ 422/534
  See application file for complete search history.

(56) References Cited

FOREIGN PATENT DOCUMENTS

| | | |
|---|---|---|
| CN | 203947102 U | 11/2014 |
| CN | 204022828 U | 12/2014 |
| CN | 204058439 U | 12/2014 |
| CN | 105441318 A | 3/2016 |
| EP | 1676906 A1 | 7/2006 |
| TW | M551624 U | 11/2017 |
| WO | WO-99/51734 A1 | 10/1999 |

\* cited by examiner

FIXED TUBE OF NUCLEIC ACID EXTRACTION COMPONENT, AND NUCLEIC ACID EXTRACTION COMPONENT

CROSS REFERENCE TO RELATED APPLICATIONS

This application claims the benefit of CN Patent Application No. 201710519911.9 entitled FIXED TUBE OF NUCLEIC ACID EXTRACTION COMPONENT, AND NUCLEIC ACID EXTRACTION COMPONENT.

BACKGROUND

Technology Field

The invention relates to a fixed tube and, in particular, to a fixed tube of a nucleic acid extraction component and a nucleic acid extraction component.

Description of Related Art

With the advancement of human genome sequencing technology, the advance in biomedical analysis technology, and the development of big data analysis tools, the era of precision medicine has arrived. The precision medicine is a customized medical model based on human genome information, combined with related internal environmental information such as proteome and metabolome, to design optimal treatment plans for patients to maximize therapeutic effects and minimize side effects.

Blood is a red opaque viscous liquid that flows through the blood vessels and heart of the human body. The main contents of blood include plasma, blood cells, and genetic material (chromosomes and genes). Among them, cfDNA (cell free DNA) are degraded DNA fragments found in plasma that are freely circulating in the blood stream, and ctDNA are circulating tumor DNA, which refers to DNA fragments in cfDNA released from a tumor.

Almost everyone's blood contains free DNA fragments (cfDNA), which may be derived from cell apoptosis or necrosis, or may enter the blood by active release (severe exercise). However, the amount of cfDNA in the blood is very low. In 1 ml of plasma, the amount of cfDNA is between about 1 ng and 100 ng, and the amount of ctDNA is much lower, which is only 0.1%~5% of cfDNA.

Some studies have indicated that the total amount of cfDNA in peripheral blood of patients with tumors is higher than that of healthy people. Based on these studies, if the amount of cfDNA is increased, it can be a good indication as a means for screening tumors. Therefore, the purification of a liquid biopsy to obtain a very small amount of cfDNA (a type of nucleic acid) is the first step in precision medicine.

In the manual purification procedure for liquid biopsy to obtain cell free nucleic acid, a very small amount of nucleic acid, is generally extracted from the sample through a silica gel membrane in a column system. In order to obtain more nucleic acids, the conventional art is to use a small volume (e.g. 0.7 ml) of membrane column and to operate the purification procedure for multiple times, or to increase the size of the membrane column so as to obtain more nucleic acids in one operation with the larger volume (e.g. more than 10 ml) of membrane column and the corresponding larger silica gel membrane. However, the first method will consume a considerable amount of operating time and cost. The second method can obtain a larger amount of nucleic acids in one operation, but the silica gel membrane of the large membrane column is enlarged and thickened, so that more solution is required for eluting the nucleic acids from the silica gel membrane. Thus, the concentration of the obtained cell free nucleic acids will be reduced.

SUMMARY

An objective of this invention is to provide a fixed tube of a nucleic acid extraction component and a nucleic acid extraction component. Compared with the above-mentioned conventional art, the design of the nucleic acid extraction component of this invention can quickly and conveniently extract high concentration nucleic acids from a large volume of sample.

The present invention discloses a fixed tube of a nucleic acid extraction component. The nucleic acid extraction component comprises a membrane column fitted in the fixed tube. The fixed tube comprises a tube body, a tube opening portion, and a bottom portion. The tube body extends along a first direction. One end of the tube opening portion distal from the tube body is provided with a protrusion, which protrudes along a second direction, and the first direction is perpendicular to the second direction. The bottom portion and the tube opening portion are respectively connected to two opposite sides of the tube body. The bottom portion is provided with a shoulder, and the shoulder of the bottom portion is connected to the membrane column.

In one embodiment, each of two opposite sides of the tube opening portion is configured with a plurality of first openings, and the plurality of first openings of the tube opening portion divide the protrusion into two sections.

In one embodiment, the bottom portion further comprises a stepwise structure and a second opening, the stepwise structure extends from the second opening of the bottom portion along the first direction, the stepwise structure is connected with the membrane column, and the membrane column protrudes beyond the fixed tube through the stepwise structure.

In one embodiment, a diameter of the tube body is greater than a diameter of the stepwise structure.

In one embodiment, a diameter of the stepwise structure is gradually decreased in a direction departing from the tube body.

In one embodiment, the tube body is configured with a third opening, and the third opening of the tube body extends along the first direction from one of the plurality of first openings of the tube opening portion to the stepwise structure.

In one embodiment, the fixed tube comprises a third opening, and the third opening of the fixed tube extends along the first direction from the tube opening portion to the stepwise structure.

In one embodiment, the membrane column comprises a first top portion, and the shoulder of the fixed tube is fitted over an outer periphery of the first top portion of the membrane column.

The present invention also discloses a nucleic acid extraction component, which comprises a membrane column and the above-mentioned fixed tube.

In one embodiment, the protrusion of the fixed tube contacts against an opening of a centrifugal tube.

As mentioned above, in the fixed tube of a nucleic acid extraction component and the nucleic acid extraction component of this invention, one end of the tube opening portion of the fixed tube distal from the tube body is provided with a protrusion. This configuration allows the operator to easily retrieve the fixed tube from the centrifugal tube. In addition, due to the design of the bottom portion of the fixed tube, the membrane column does not fall in the bottom of the centrifugal tube during the centrifugal operation, so that the sample will not be spilled from the membrane column, thereby increasing the success rate of the operation. In addition, the design of the fixed tube and the membrane column of the nucleic acid extraction component of this invention can quickly and conveniently extract high concentration nucleic acids from a large volume of sample.

In one embodiment of this invention, the design of the plurality of first openings of the tube opening portion can divide the protrusion into two sections, so that the operation of the extraction procedure can be easier.

BRIEF DESCRIPTION OF THE DRAWINGS

The invention will become more fully understood from the detailed description and accompanying drawings.

DETAILED DESCRIPTION OF THE INVENTION

The fixed tube of a nucleic acid extraction component and the nucleic acid extraction component of this invention will be apparent from the following embodiments with reference to the accompanying drawings, wherein the same references relate to the same elements.

In the nucleic acid purification process of liquid biopsy, the present invention extracts a very small amount of nucleic acid from a sample by a centrifuge machine with using a nucleic acid extraction component. The sample may be, for example but not limited to, blood, plasma, urine or tissue fluid. In addition, the nucleic acid extraction component of the invention can quickly and conveniently extract the larger volume of sample to obtain the high yield and high concentration nucleic acid without multiple extraction operations and enlarging the membrane column or membrane. The structure and features of the nucleic acid extraction component will be described in the following embodiments.

Figure 1:
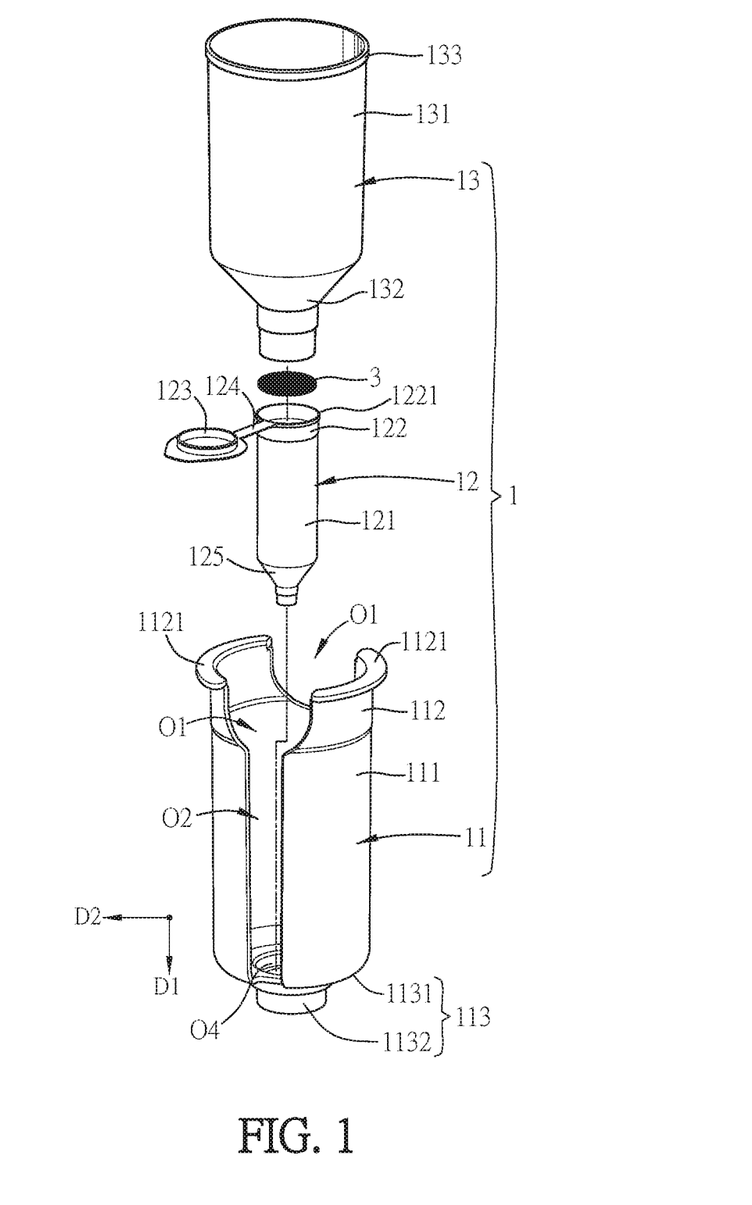
FIGS. 1 and 2 are exploded views of the nucleic acid extraction component according to an embodiment of this invention.
Figure 2:
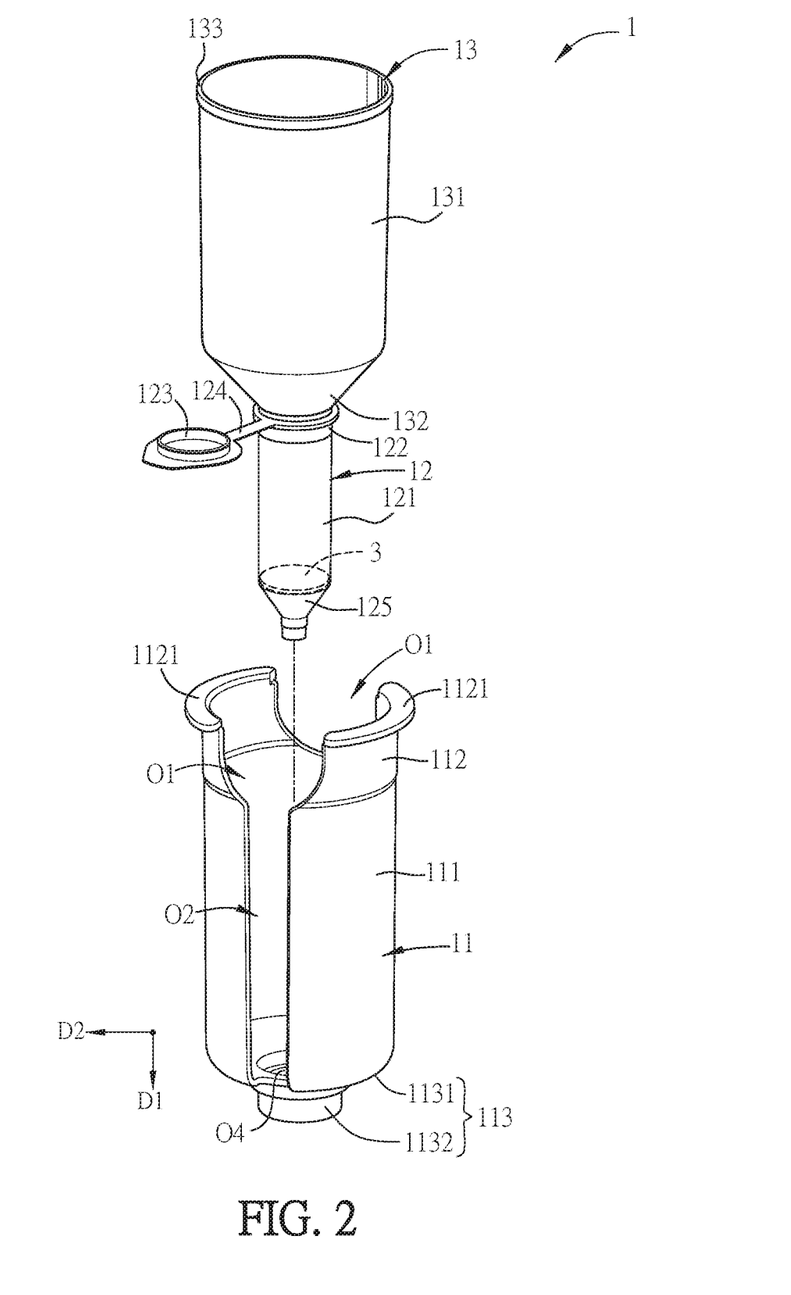
Figure 3:
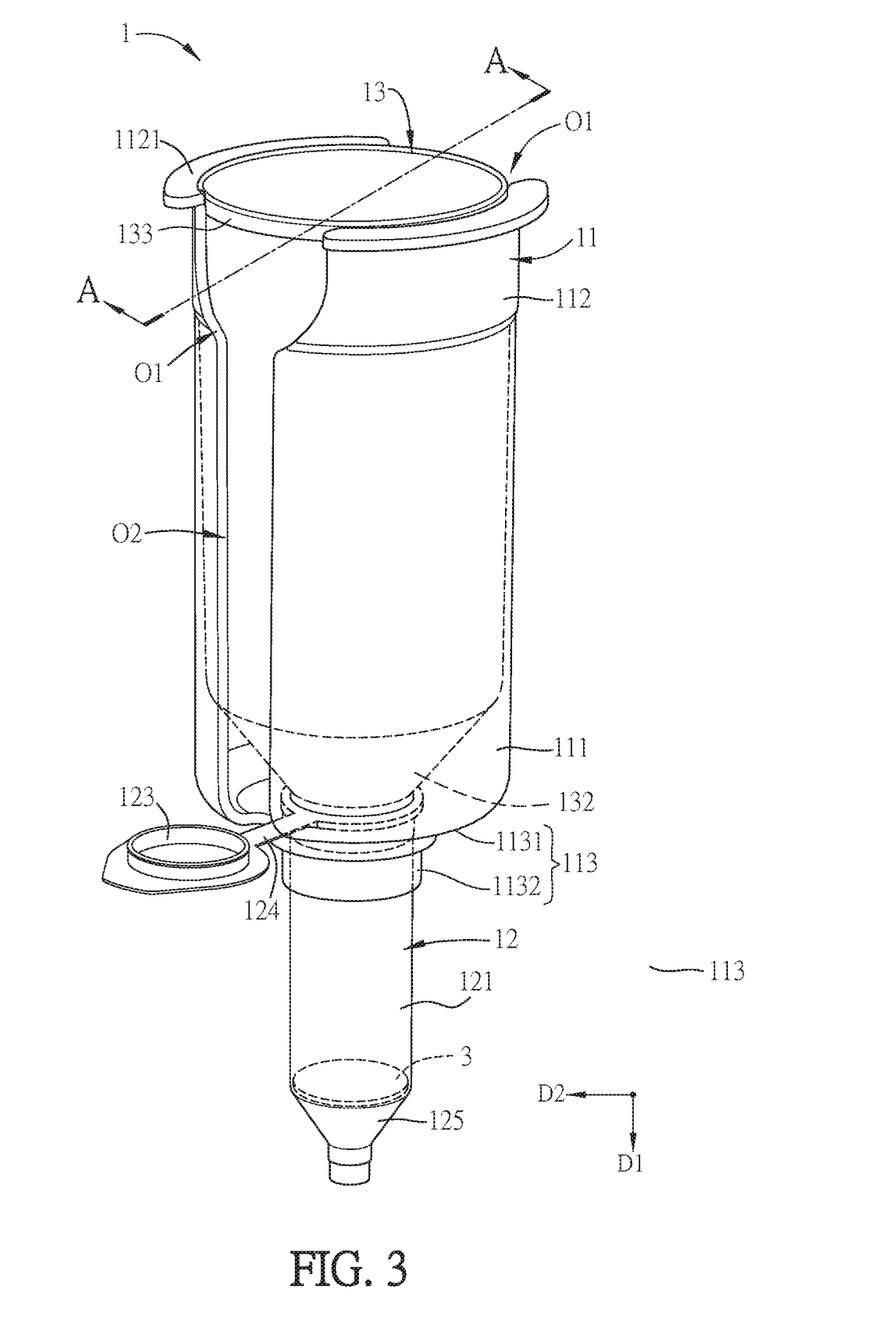
FIG. 3 is a schematic diagram showing the assembled nucleic acid extraction component according to an embodiment of this invention.
Figure 4A:
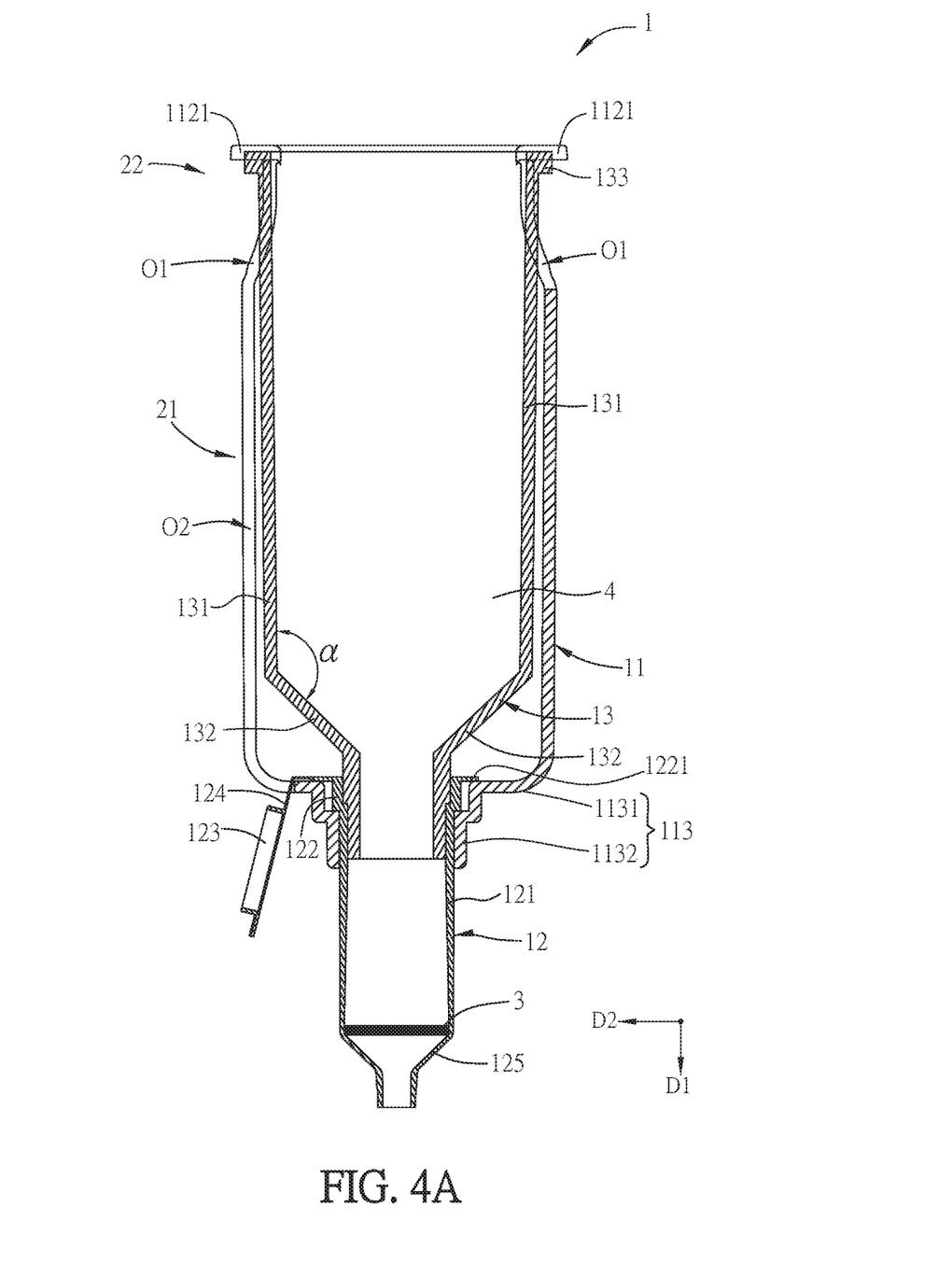
FIG. 4A is a sectional view of the nucleic acid extraction component of FIG. 3 along the line A-A.

Please refer to FIGS. 1 to 4A, wherein FIGS. 1 and 2 are exploded views of the nucleic acid extraction component according to an embodiment of this invention, FIG. 3 is a schematic diagram showing the assembled nucleic acid extraction component according to an embodiment of this invention, and FIG. 4A is a sectional view of the nucleic acid extraction component of FIG. 3 along the line A-A.

As shown in FIGS. 1 to 4A, the nucleic acid extraction component 1 comprises a fixed tube 11 and a membrane column 12. In this embodiment, a membrane 3 is provided inside the membrane column 12. In addition, the nucleic acid extraction component 1 of this embodiment can further comprise an inner tube 13.

The membrane column 12 is fitted in the fixed tube 11. In this embodiment, the membrane column 12 is connected to the inner tube 13 and fitted in the fixed tube 11, and a part of the membrane column 12 is protruded beyond the fixed tube 11. Herein, the fixed tube 11, the membrane column 12 and the inner tube 13 are substantially cylindrical tubes, and the materials of the fixed tube 11, the membrane column 12 and the inner tube 13 are, for example but not limited to, plastic materials. In addition, the capacities and sizes of the fixed tube 11, the membrane column 12 and the inner tube 13 are not limited in this invention, and any configuration that the fixed tube 11, the membrane column 12 and the inner tube 13 can matched with each other is acceptable. In some embodiments, for example, the capacity of the membrane column 12 is between 0.5 ml and 1 ml, so that the membrane column 12 can only contain a few amount of sample. Of course, the membrane 3 configured inside the membrane column 12 is also very small. In some embodiments, the capacity of the inner tube 13 is larger, which may contain the sample of more than 10 ml. Accordingly, when the sample solution contained in the membrane column 12 flows through the membrane 3, the sample contained in the inner tube 13 can be added to the membrane column 12. Since the inner tube 13 contains more sample volume, the membrane 3 can absorb more amount of nucleic acids after the centrifugal process, thereby extracting high concentration nucleic acid. Moreover, the membrane column 12 and the inner tube 13 of this embodiment are two separated members, but this invention is not limited thereto. In some embodiments, the membrane column 12 and the inner tube 13 can be integrally formed as a single structure, and this invention is not limited.

The fixed tube 11 comprises a tube body 111, a tube opening portion 112, and a bottom portion 113. The tube body 111 extends along a first direction D1, and the bottom portion 113 and the tube opening portion 112 are respectively connected to two opposite sides of the tube body 111. One end of the tube opening portion 112 distal from the tube body 111 is provided with a protrusion 1121, which protrudes along a second direction D2. The first direction D1 is perpendicular to the second direction D2. Moreover, in this embodiment, the bottom portion 113 is provided with a shoulder 1131, a stepwise structure 1132, and a second opening O4. In this case, the diameter of the tube body 111 is greater than the diameter of the stepwise structure 1132, and the shoulder 1131 of the bottom portion 113 is connected to the membrane column 12. The stepwise structure 1132 extends from the second opening O4 of the bottom portion 113 along the first direction D1. The stepwise structure 1132 is connected with the membrane column 12, and the membrane column 12 protrudes beyond the fixed tube 11 through the stepwise structure 1132. In this embodiment, the membrane column 12 protrudes beyond the fixed tube 11 through the second opening 4 of the bottom portion 113.

In this embodiment, each of two opposite sides of the tube opening portion 112 is configured with a plurality of first openings O1, and the plurality of first openings O1 of the tube opening portion 112 divide the protrusion 1121 into two sections. Herein, an included angle is formed between the first direction D1 and the second direction D2. In this embodiment, the included angle between the first direction D1 and the second direction D2 can be, for example but not limited to, 90 degrees. In different embodiments, the included angle between the first direction D1 and the second direction D2 can be greater than 90 degrees (e.g. 120 degrees) or less than 90 degrees (e.g. 75 degrees), and this invention is not limited thereto. Specifically, two first openings O1 are formed at two opposite sides of the tube opening portion 112, respectively, so that the tube opening portion 112 and the protrusion 1121 can be divided into two sections. This configuration is benefit to the following operation. In addition, the diameter of the stepwise structure 1132 is gradually decreased in a direction departing from the tube body 111. That is, the part of the stepwise structure located farer away from the tube body 111 has a smaller diameter. Thus, when the membrane column 12 is connected with the inner tube 13 and fitted inside the fixed tube 11, the membrane column 12 and the inner tube 13 can be fixed, so that the membrane column 12 will not be separated from the inner tube 13.

Figure 5A:
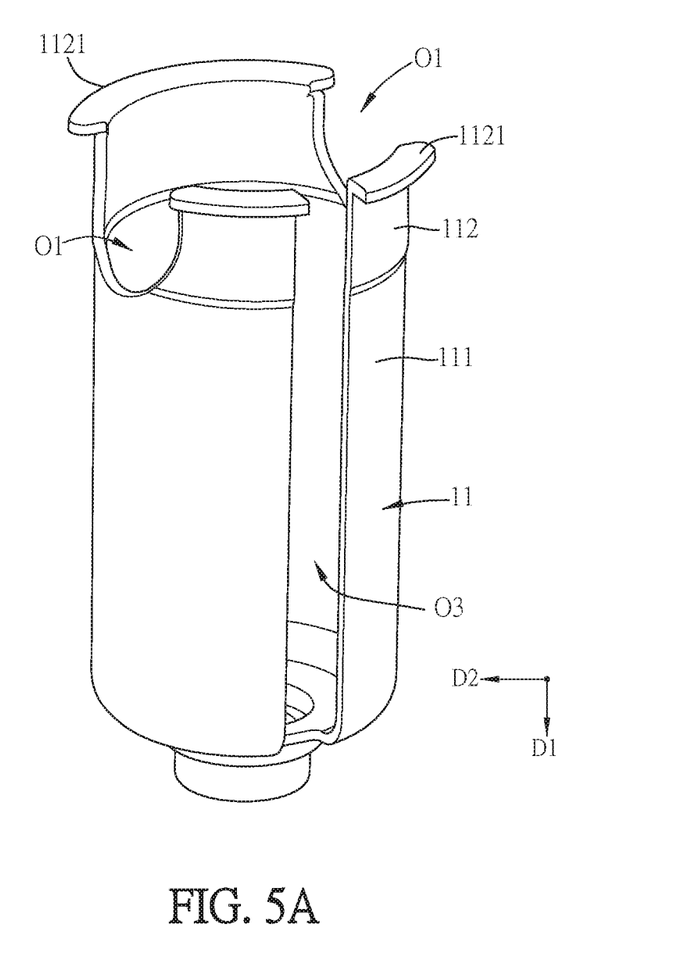
FIGS. 5A and 5B are schematic diagrams showing the fixed tubes according to different embodiments of this invention.
Figure 5B:
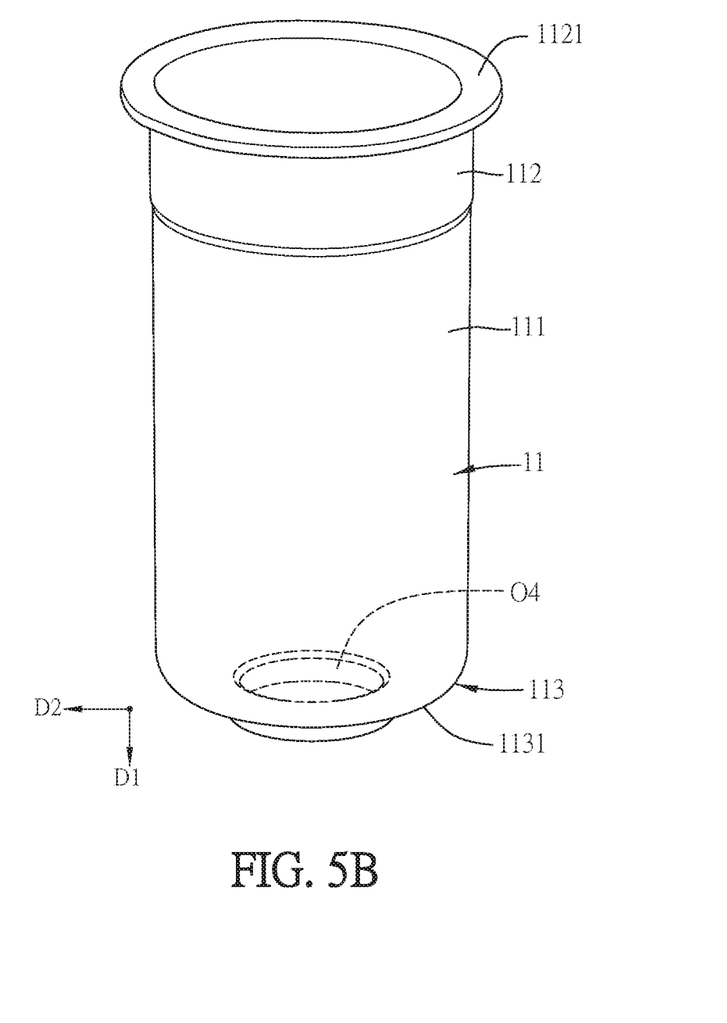

One side of the tube body 111 is configured with a third opening O2, and the third opening O2 of the tube body 111 extends along the first direction D1 from one of the plurality of first openings O1 of the tube opening portion 112 to the stepwise structure 1132. In different embodiments, an additional opening of the tube body 111 (not shown) can be formed at the other side of the tube body 111 opposite to the above-mentioned third opening O2 of the tube body 111. The additional opening of the tube body 111 can also extend along the first direction D1 from the other one of the plurality of first openings O1 of the tube opening portion 112. Alternatively, as shown in FIG. 5A, except the plurality of first openings O1 of the tube opening portion 112, the fixed tube 11 is configured without the third opening O2 of the tube body 111 but is configured with a third opening O3. The third opening O3 of the fixed tube 11 extends along the first direction D1 from the protrusion 1121 of the tube opening portion 112 to the stepwise structure 1132. In some embodiments, the fixed tube 11 can be configured without the plurality of first openings O1 of the tube opening portion 112, the third opening O2 of the tube body 111, the third opening O3 of the fixed tube 11, and the stepwise structure 1132. As shown in FIG. 5B, the bottom portion 113 of the fixed tube 11 of this embodiment is configured with a shoulder 1131 and a second opening O4 of the bottom portion 113, but is configured without the stepwise structure 1132, the plurality of first openings O1 of the tube opening portion 112, the third opening O2 of the tube body 111, and the third opening O3 of the fixed tube 11. Alternatively, in other embodiments, the fixed tube 11 can be configured without the plurality of first openings O1 of the tube opening portion 112, the third opening O2 of the tube body 111, and/or the third opening O3 of the fixed tube 11, but can be configured with the stepwise structure 1132. In other embodiments, the fixed tube 11 can be configured without the stepwise structure 1132, but can be configured with the plurality of first openings O1 of the tube opening portion 112, the third opening O2 of the tube body 111, and/or the third opening O3 of the fixed tube 11. This invention is not limited thereto.

The membrane column 12 comprises a cylindrical tube portion 121, a first top portion 122 and a first bottom portion 125. The cylindrical tube portion 121 extends along a first direction D1, and the first top portion 122 and the first bottom portion 125 are connected with the opposite sides of the cylindrical tube portion 121, respectively. In this embodiment, the first top portion 122 of the membrane column 12 has a ring shape, and the first bottom portion 125 has a funnel shape. As shown in FIG. 3, the first bottom portion 125 and a part of the cylindrical tube portion 121 are protruded beyond the bottom portion 113 of the fixed tube 11. In addition, as shown in FIG. 4A, the bottom portion 113 of the fixed tube 11 is connected with the first top portion 122 of the membrane column 12, and the first bottom portion 125 of the membrane column 12 is protruded beyond the fixed tube 11 through the second opening O4 of the bottom portion 113. Of course, in different embodiments, the membrane column 12 may not protrude beyond the fixed tube 11. For example, the cylindrical tube portion 121 can be leveled with the bottom portion 113, or the cylindrical tube portion 121 can be sunk inside the bottom portion 113. This invention is not limited thereto.

Specifically, in order to fix the membrane column 12 by the fixed tube 11, the diameter of the bottom portion 113 of the fixed tube 11 is configured corresponding to the diameter of the first top portion 122 of the membrane column 12, so that the shoulder 1131 of the fixed tube 11 can be fitted cover the outer periphery of the first top portion 122 of the membrane column 12. As shown in FIG. 4A, the extension portion 1221 of the first top portion 122 of the membrane column 12 is engaged with the shoulder 1131 of the fixed tube 11. Thus, the lower edge of the first top portion 122 of the membrane column 12 can be engaged with the stepwise structure 1132 of the bottom portion 113 of the fixed tube 11, thereby connecting the bottom portion 113 to the first top portion 122 of the membrane column 12. To be noted, in some embodiments, the diameter of the bottom portion 113 of the fixed tube 11 can be not configured corresponding to the diameter of the first top portion 122 of the membrane column 12, or they can be not tightly engaged. For example, the lower edge of the first top portion 122 of the membrane column 12 can be engaged to the shoulder 1131 of the fixed tube 11 for connecting the membrane column 12 to the fixed tube 11, and this invention is not limited. In addition, the membrane column 12 of this embodiment further comprises a tube cap 123 and a connecting portion 124. The connecting portion 124 connects the tube cap 123 to the first top portion 122 of the membrane column 12. In this embodiment, the tube cap 123 is configured to cover the first top portion 122 of the membrane column 12. Therefore, when the sample is placed inside the membrane column 12, the tube cap 123 can prevent the overflow of the sample (in practice, the tube cap 123 will be opened when extracting the nucleic acid).

Figure 6:
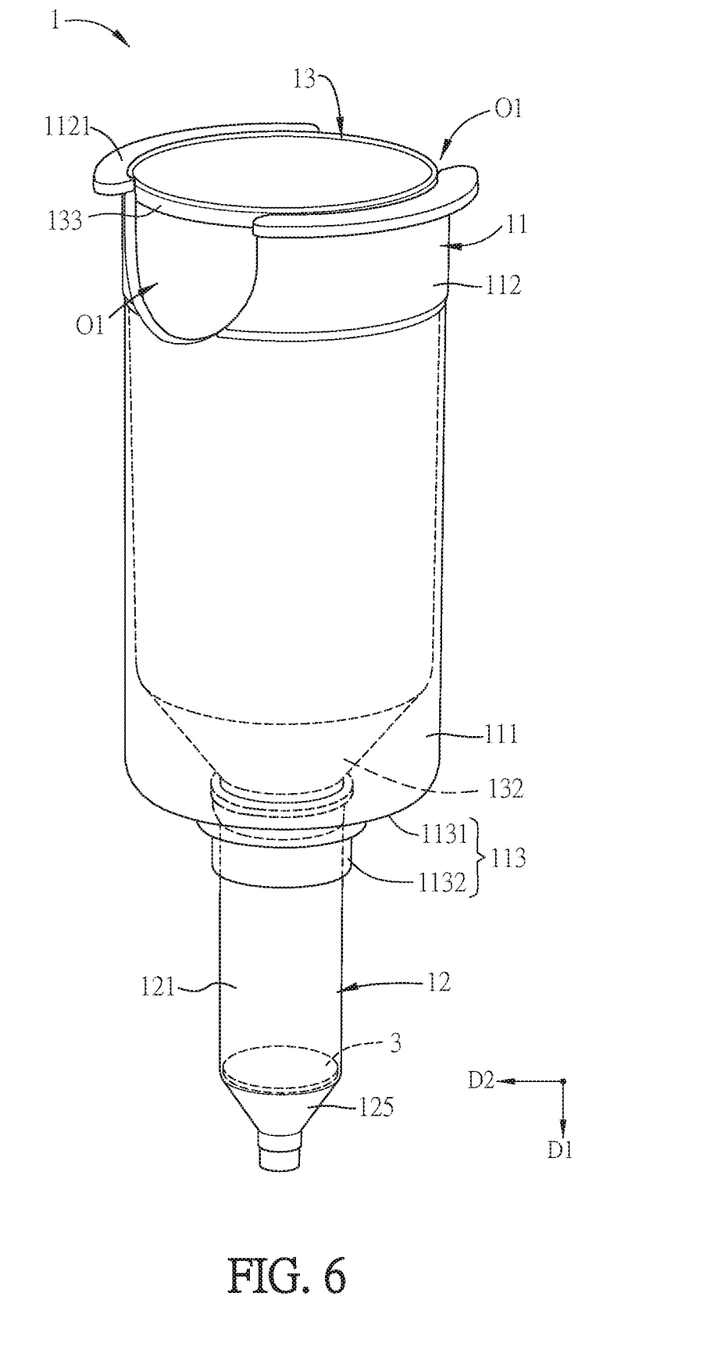
FIG. 6 is a schematic diagram showing the assembled nucleic acid extraction component according to another embodiment of this invention.

In addition, with reference to FIG. 3, in this embodiment, since the tube body 111 is configured with a third opening O2, when the membrane column 12 is disposed in the fixed tube 11, the tube cap 123 can be moved downwardly from one of the plurality of first openings O1 of the tube opening portion 112 to the shoulder 1131 through the third opening O2 of the tube body 111. Accordingly, the membrane column 12 can be disposed inside the fixe tube 11, and the first bottom portion 125 and a part of the cylindrical tube portion 121 of the membrane column 12 can be protruded beyond the fixed tube 11 through the second opening O4 of the bottom portion 113, thereby connecting the first top portion 122 of the membrane column 12 to the stepwise structure 1132. In other embodiments, as shown in FIG. 6, if the membrane column 12 is configured without the tube cap 123 and the connecting portion 124, the third opening O2 of the tube body 111 is not needed.

Figure 4B:
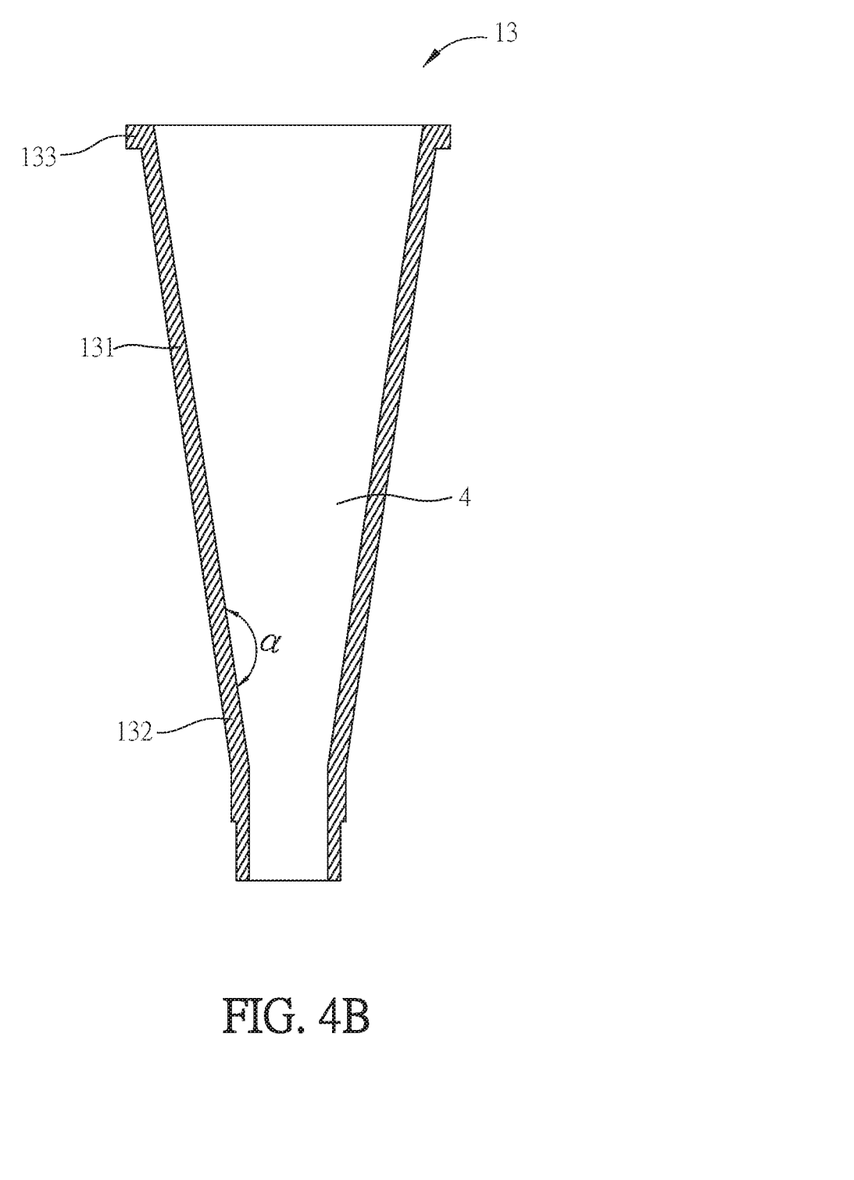
FIG. 4B is a sectional view of an inner tube according to another embodiment of this invention.

In this embodiment, the inner tube 13 comprises a cylindrical tube portion 131, a second bottom portion 132 and a second top portion 133. The cylindrical tube portion 131 also extends along the first direction D1, and the second bottom portion 132 and the first top portion 133 are connected with the opposite sides of the cylindrical tube portion 131, respectively. In this embodiment, the second top portion 133 has a ring shape, and the second bottom portion 132 has a funnel shape. The diameter thereof is corresponding to the diameter of the first top portion 122 of the membrane column 12, so that the second bottom portion 132 of the inner tube 13 can be inserted into the first top portion 122 of the membrane column 12 when connecting the inner tube 13 to the membrane column 12. Accordingly, the sample can flow from the inner tube 13 to the membrane column 12. Moreover, in this embodiment, when the membrane column 12 is connected to the inner tube 13 and is fitted inside the fixed tube 11, a part of the second bottom portion 132 of the inner tube 13 can be inserted into the membrane column 12 through the first top portion 122. Thus, the first top portion 122 of the membrane column 12 can be fitted over the outer periphery of the second bottom portion 132 of the inner tube 13, and then the inner tube 13 is disposed inside the fixed tube 11. As shown in FIGS. 4A and 4B, the included angle α between the second bottom portion 132 and the cylindrical tube portion 131 can be greater than 157 degrees (as shown in FIG. 4A) and be less than or equal to 180 degrees (as shown in FIG. 4B). This configuration can prevent the residual sample around the included angle α, thereby further improving the extraction efficiency of the nucleic acid extraction component 1. In addition, the inner tube 13 of this embodiment is not configured with the tube cap. However, in other embodiments, the inner tube 13 can be configured with a tube cap (not shown) for covering the second top portion 133, and this invention is not limited.

The membrane 3 is disposed inside the membrane column 12 and is located adjacent to the first bottom portion 125. In some embodiments, the membrane 3 is, for example but not limited to, a silica membrane. The membrane 3 can carry positive charges, and the nucleic acids in the sample can carry negative charges after a pretreatment process. Accordingly, the nucleic acids can be attached to the membrane 3 due to the attraction of the positive and negative charges during the centrifugal process, and then the nucleic acids attached to the membrane 3 can be extracted in the following process.

As mentioned above, in the nucleic acid extraction component 1 of this embodiment, one end of the tube opening portion 112 distal from the tube body 111 is provided with a protrusion 1121 protruding along the second direction D2. This configuration allows the operator to easily retrieve the fixed tube 11. In addition, the design of the shoulder 1131 of the bottom portion 113 of the fixed tube 11 can be engaged with the membrane column 12, so that the sample will not be spilled from the membrane column 12 or the inner tube 13 during the centrifugal process, thereby increasing the success rate of the operation (if the membrane column 12 is not engaged, it may detach from the fixed tube 11 during the centrifugal process, so that the sample may be spilled from the membrane column 12 and will not pass through the membrane 3, resulting in the failure of the centrifugal process). In addition, the configuration of the plurality of first openings O1 of the tube opening portion 112 can divide the protrusion 1121 into two sections, so that the extraction operation is easier. For example, this design makes it easier to place the membrane column 12 and the inner tube 13 into the fixed tube 11, and to take the membrane column 12 and the inner tube 13 out of the fixed tube 11. In addition, since the inner tube 13 has a larger capacity for accommodating more sample but the size of the membrane 3 is remained, the structural design of the nucleic acid extraction component 1 can quickly and conveniently extract larger yield and higher concentration of nucleic acid.

Figure 7:
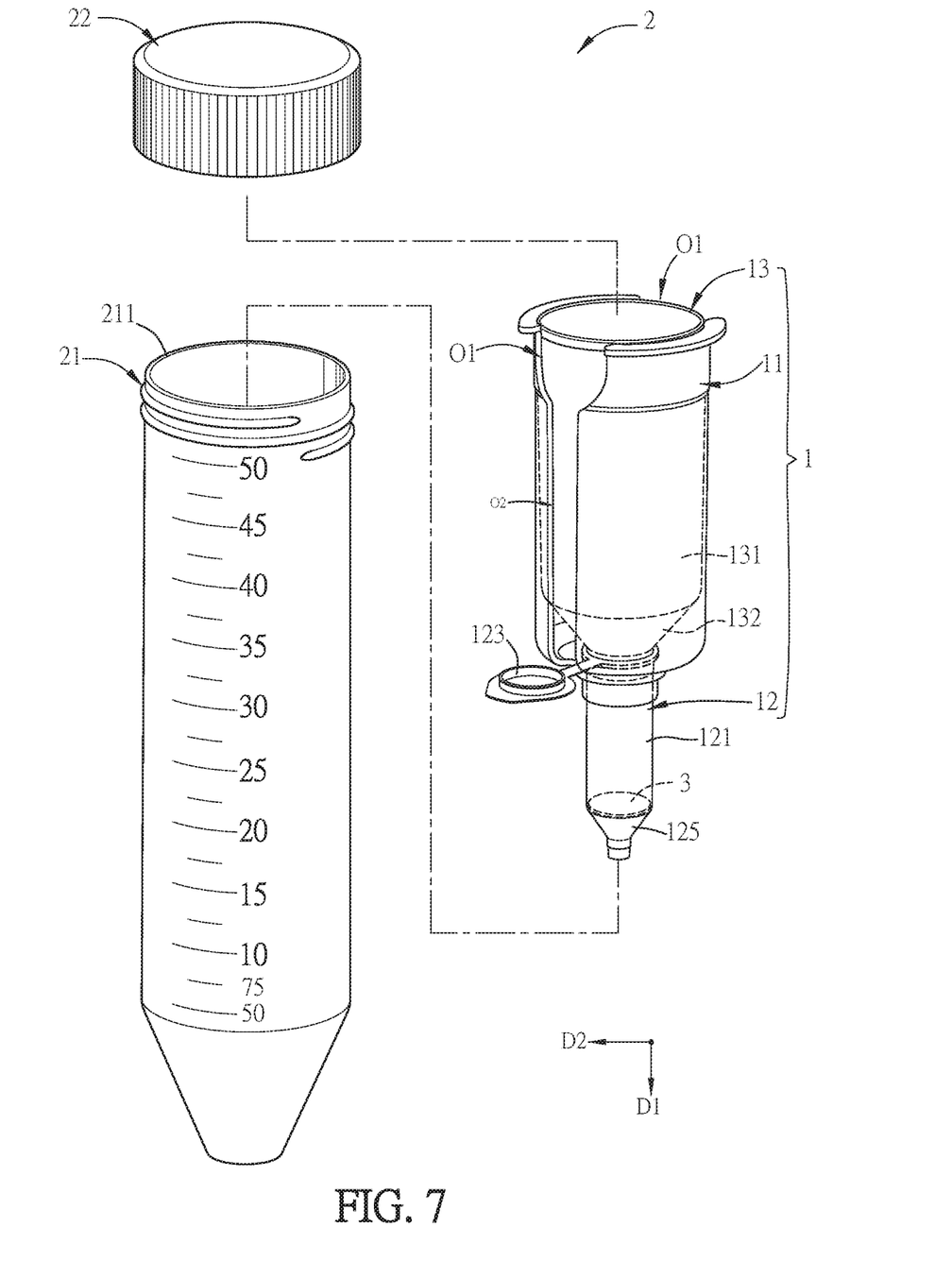
FIGS. 7 and 8 are an exploded view and an assembled view of a centrifugal component according to an embodiment of this invention.
Figure 8:
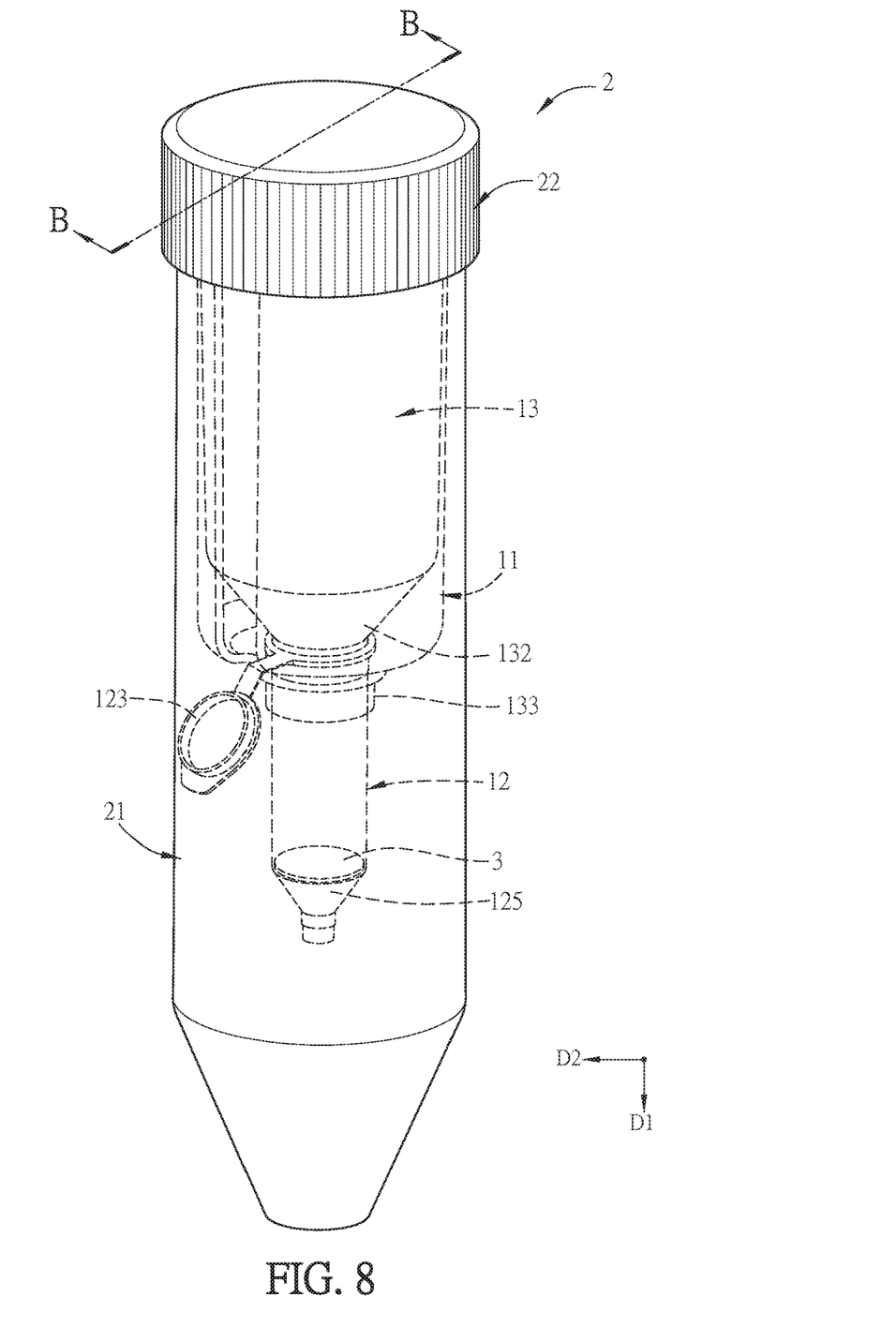
Figure 9:
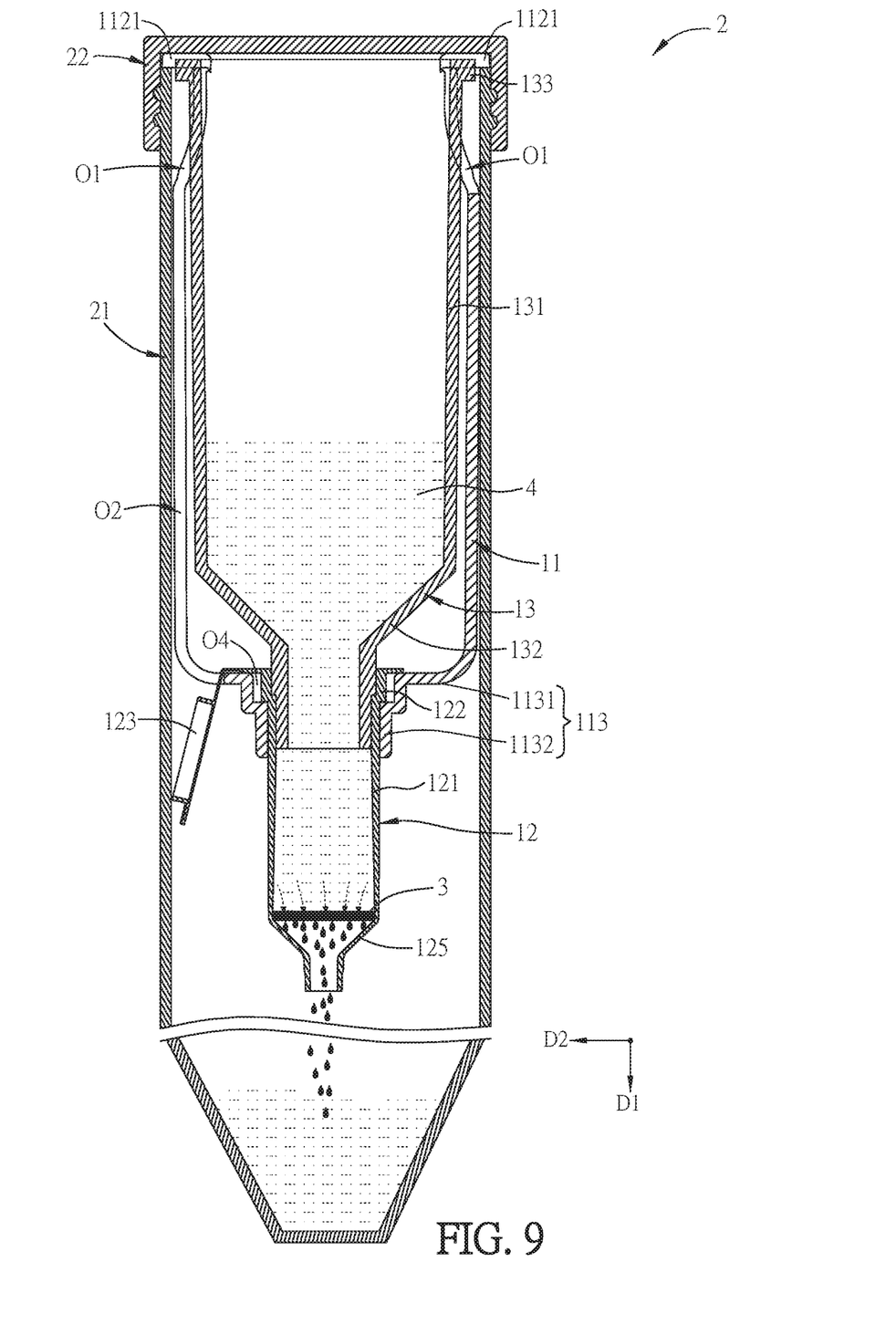
FIG. 9 is a sectional view of the centrifugal component of FIG. 8 along the line B-B.

Please refer to FIGS. 7 to 9, wherein FIGS. 7 and 8 are an exploded view and an assembled view of a centrifugal component 2 according to an embodiment of this invention, and FIG. 9 is a sectional view of the centrifugal component 2 of FIG. 8 along the line B-B.

In this embodiment, the centrifugal component 2 comprises a nucleic acid extraction component 1, a centrifugal tube 21 and a tube cap 22. The specific technical features and modifications of the nucleic acid extraction component 1 can be referred to the above embodiments, so the detailed description thereof will be omitted.

In some embodiments, the capacity of the centrifugal tube 21 is, for example but not limited to, 50 ml. In practice, the membrane column 12 is connected to the inner tube 13 and then fitted in the fixed tube 11 so as to form the nucleic acid extraction component 1. Afterwards, the sample 4 is added into the inner tube 13 and the membrane column 12. In this case, the inner tube 13 has a larger capacity (e.g. more than 10 ml) for accommodating more sample 4. Next, the nucleic acid extraction component 1 is placed into the centrifugal tube 21, so that the protrusion 1121 of the fixed tube 11 contacts against the tube opening 211 of the centrifugal tube 21, thereby installing the fixed tube 11 in the centrifugal tube 21. After closing the tube cap 22 to cover the centrifugal tube 21 (by, for example but not limited to, locking), the entire centrifugal component 2 is disposed in the centrifuge machine. Then, the sample 4 can pass through the membrane 3 in the centrifugal process, and the nucleic acids in the sample 4 can be absorbed by the membrane 3, thereby extracting the nucleic acids from the sample 4.

In the conventional art of extracting the nucleic acids, the inner tube 13 and the fixed tube 11 are not used. In addition, the capacity of the membrane column 12 is very small. Accordingly, it is needed to perform multiple operations for extracting a certain amount of nucleic acids, which will cause a lot of operation time and cost. If it is desired to obtain the required amount of nucleic acids in one operation, the size of the membrane column must be enlarged (e.g. more than 10 ml) for accommodating more sample, and a large-sized membrane is also needed for the enlarged membrane column.

However, the above-mentioned method has the following three drawbacks. (1) When a large-sized membrane is used to obtain the same amount of nucleic acids, the nucleic acids will be distributed on and attached to the large-sized membrane, but the solution (e.g. pure water) for eluting the membrane may not cover the entire membrane, which can cause the low recovery rate of the nucleic acids. (2) If more solution is provided to eluting the membrane, the concentration of the nucleic acid will be diluted, which may affect the following detection reaction (e.g. the NGS reaction). (3) In order to make the nucleic acids to carry negative charges, the pretreatment process for the sample is needed. However, the cleavage solution used in the pretreatment process contains a high concentration of salt, and even after washing with the washing solution, a small amount of salt still remains on the membrane. When the membrane is too large, the amount of the remained salts is increased, and the remained salts will interfere the results of the following PCR (polymerization chain reaction).

In this embodiment, the multiple operation with the centrifugal component 2 is not needed, and the structure design of the fixed tube 11, the membrane column 12 and the inner tube 13 of the nucleic acid extraction component 1 can accommodate a larger amount of sample without enlarging the membrane column 12. In addition, the amount of nucleic acids in the liquid biopsy is very small and is far less than the maximum absorption amount of the membrane 3, so that the enlarged membrane 3 is not needed. Accordingly, the high yield of nucleic acids can be obtained by one operation. Therefore, this invention does not have the above three drawbacks, and can elute the membrane to obtain the nucleic acids with a fewer amount of solution. Compared with the conventional art, this invention only needs one extraction operation to obtain the higher yield and higher concentration nucleic acids.

To be noted, in the above embodiment, the membrane column 12 is supported by the fixed tube 11. In order to perform the following elution process for obtaining the nucleic acids easier, the membrane column 12 can be took out of the fixed tube 11 and then placed in a collection tube (e.g. 2 ml), followed by the steps of washing, drying and elution. Accordingly, the membrane column 12 and the fixed tube 11 of this invention can be separated, and this design makes the following three steps much easier. In addition, the sample 4 can be eluted in, for example, a 1.5 ml centrifugal tube by utilizing a smaller volume of solution, thereby increasing the concentration of the nucleic acids. Moreover, the membrane column 12 can be easily stored for the operation next time.

As mentioned above, in the fixed tube of a nucleic acid extraction component and the nucleic acid extraction component of this invention, one end of the tube opening portion of the fixed tube distal from the tube body is provided with a protrusion. This configuration allows the operator to easily retrieve the fixed tube from the centrifugal tube. In addition, due to the design of the bottom portion of the fixed tube, the membrane column does not separate from the inner tube during the centrifugal operation, so that the sample will not be spilled from the membrane column, thereby increasing the success rate of the operation. In addition, the design of the fixed tube and the membrane column of the nucleic acid extraction component of this invention can quickly and conveniently extract high yield and high concentration nucleic acids from a large volume of sample.

In one embodiment of this invention, the design of the plurality of first openings of the tube opening portion can divide the protrusion into two sections, so that the operation of the extraction procedure can be easier.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. A fixed tube of a nucleic acid extraction component, wherein the nucleic acid extraction component comprises a membrane column fitted in the fixed tube, wherein the fixed tube comprises:
   a tube body extending along a first direction;
   a tube opening portion, wherein one end of the tube opening portion distal from the tube body is provided with a protrusion, which protrudes along a second direction, and the first direction is perpendicular to the second direction; and
   a bottom portion, wherein the bottom portion and the tube opening portion are respectively connected to two opposite sides of the tube body, the bottom portion is provided with a shoulder, and the shoulder of the bottom portion is connected to the membrane column,
   wherein each of two opposite sides of the tube opening portion is configured with a plurality of first openings, and the plurality of first openings divide the protrusion into two sections,
   wherein the bottom portion further comprises a stepwise structure and a second opening, the stepwise structure extends from the second opening along the first direction, the stepwise structure is connected with the membrane column, and the membrane column protrudes beyond the fixed tube through the stepwise structure.

2. The fixed tube of claim 1, wherein a diameter of the tube body is greater than a diameter of the stepwise structure.

3. The fixed tube of claim 1, wherein a diameter of the stepwise structure is gradually decreased in a direction departing from the tube body.

4. The fixed tube of claim 1, wherein the tube body is configured with a third opening, and the third opening of the tube body extends along the first direction from one of the plurality of first openings to the stepwise structure.

5. The fixed tube of claim 1, wherein the fixed tube comprises a third opening, and the third opening of the fixed tube extends along the first direction from the tube opening portion to the stepwise structure.

6. The fixed tube of claim 1, wherein the membrane column comprises a first top portion, and the shoulder of the fixed tube is fitted over an outer periphery of the first top portion of the membrane column.

7. A nucleic acid extraction component, wherein the nucleic acid extraction component comprises: a silica gel membrane positioned in the membrane column; and
   the fixed tube of claim 1.

8. The nucleic acid extraction component of claim 7, wherein the protrusion of the fixed tube contacts against an opening of a centrifugal tube.

9. The nucleic acid extraction component of claim 7, wherein a diameter of the tube body is greater than a diameter of the stepwise structure.

10. The nucleic acid extraction component of claim 7, wherein a diameter of the stepwise structure is gradually decreased in a direction departing from the tube body.

11. The nucleic acid extraction component of claim 7, wherein the tube body is configured with a third opening, and the third opening of the tube body extends along the first direction from one of the plurality of first openings to the stepwise structure.

12. The nucleic acid extraction component of claim 7, wherein the fixed tube comprises a third opening, and the third opening of the fixed tube extends along the first direction from the tube opening portion to the stepwise structure.

13. The nucleic acid extraction component of claim 7, wherein the membrane column comprises a first top portion, and the shoulder of the fixed tube is fitted over an outer periphery of the first top portion of the membrane column.

* * * * *